United States Patent
Kuo et al.

(10) Patent No.: US 8,810,356 B2
(45) Date of Patent: Aug. 19, 2014

(54) DATA BUFFER APPARATUS WITH WIRELESS TRANSMISSION FUNCTION

(75) Inventors: Bo-Jau Kuo, Taipei (TW); Ching-Hsiu Yang, Taipei (TW)

(73) Assignee: National Yang Ming University, Taipei (TW)

( * ) Notice: Subject to any disclaimer, the term of this patent is extended or adjusted under 35 U.S.C. 154(b) by 350 days.

(21) Appl. No.: 12/966,731

(22) Filed: Dec. 13, 2010

(65) Prior Publication Data

US 2012/0086543 A1      Apr. 12, 2012

(30) Foreign Application Priority Data

Oct. 6, 2010   (TW) ................................ 99134047 A

(51) Int. Cl.
*G05B 23/02* (2006.01)
*A61B 5/00* (2006.01)
*G06F 19/00* (2011.01)

(52) U.S. Cl.
CPC .......... *A61B 5/0022* (2013.01); *G06F 19/3418* (2013.01); *H04W 79/02* (2013.01); *Y10S 128/90* (2013.01); *Y10S 128/903* (2013.01)
USPC ..... 340/3.31; 340/3.3; 340/3.32; 340/539.12; 340/286.07; 600/485; 600/301; 128/900; 128/903

(58) Field of Classification Search
CPC ............... A61B 5/0002; A61B 5/0022; A61B 5/02438; G06F 19/3418; G06F 19/3406; G08B 21/0211; G08B 21/0453; A01B 12/006; H04W 76/02; Y10S 128/903
USPC .............. 340/3.3, 3.31, 3.32, 539.11, 539.12, 340/286.07; 600/485, 301; 128/900, 903; 455/343.1–343.6
See application file for complete search history.

(56) References Cited

U.S. PATENT DOCUMENTS

| | | | | |
|---|---|---|---|---|
| 5,564,434 | A * | 10/1996 | Halperin et al. | 600/488 |
| 5,904,708 | A * | 5/1999 | Goedeke | 607/18 |
| 6,014,432 | A * | 1/2000 | Modney | 379/106.02 |
| 6,336,900 | B1 * | 1/2002 | Alleckson et al. | 600/485 |
| 7,061,399 | B2 * | 6/2006 | Leck | 340/870.06 |
| 8,116,245 | B2 * | 2/2012 | Kwon et al. | 370/311 |
| 8,165,893 | B1 * | 4/2012 | Goldberg et al. | 705/2 |
| 2008/0018454 | A1 * | 1/2008 | Chan et al. | 340/539.11 |
| 2008/0103554 | A1 * | 5/2008 | Dicks et al. | 607/60 |
| 2009/0076405 | A1 * | 3/2009 | Amurthur et al. | 600/529 |
| 2011/0074623 | A1 * | 3/2011 | Baker | 342/175 |

* cited by examiner

*Primary Examiner* — Nabil Syed
*Assistant Examiner* — Nay Tun
(74) *Attorney, Agent, or Firm* — Muncy, Geissler, Olds & Lowe, P.C.

(57) ABSTRACT

The present invention relates to a data buffer apparatus with wireless transmission function, including a transmission interface module, a memory module, a wireless transmission module and a microprocessor module. The transmission interface module is coupled to a monitoring unit and continuously receives at least one transmission signal data to be stored in the memory module. When the memory module has the transmission signal data, the microprocessor module controls the wireless transmission module to attempts to establish a wireless connection. If the wireless connection is successfully established, the transmission signal data will be sent. If the wireless connection can not be established, it will attempt to establish the wireless connection again after a period of time.

8 Claims, 1 Drawing Sheet

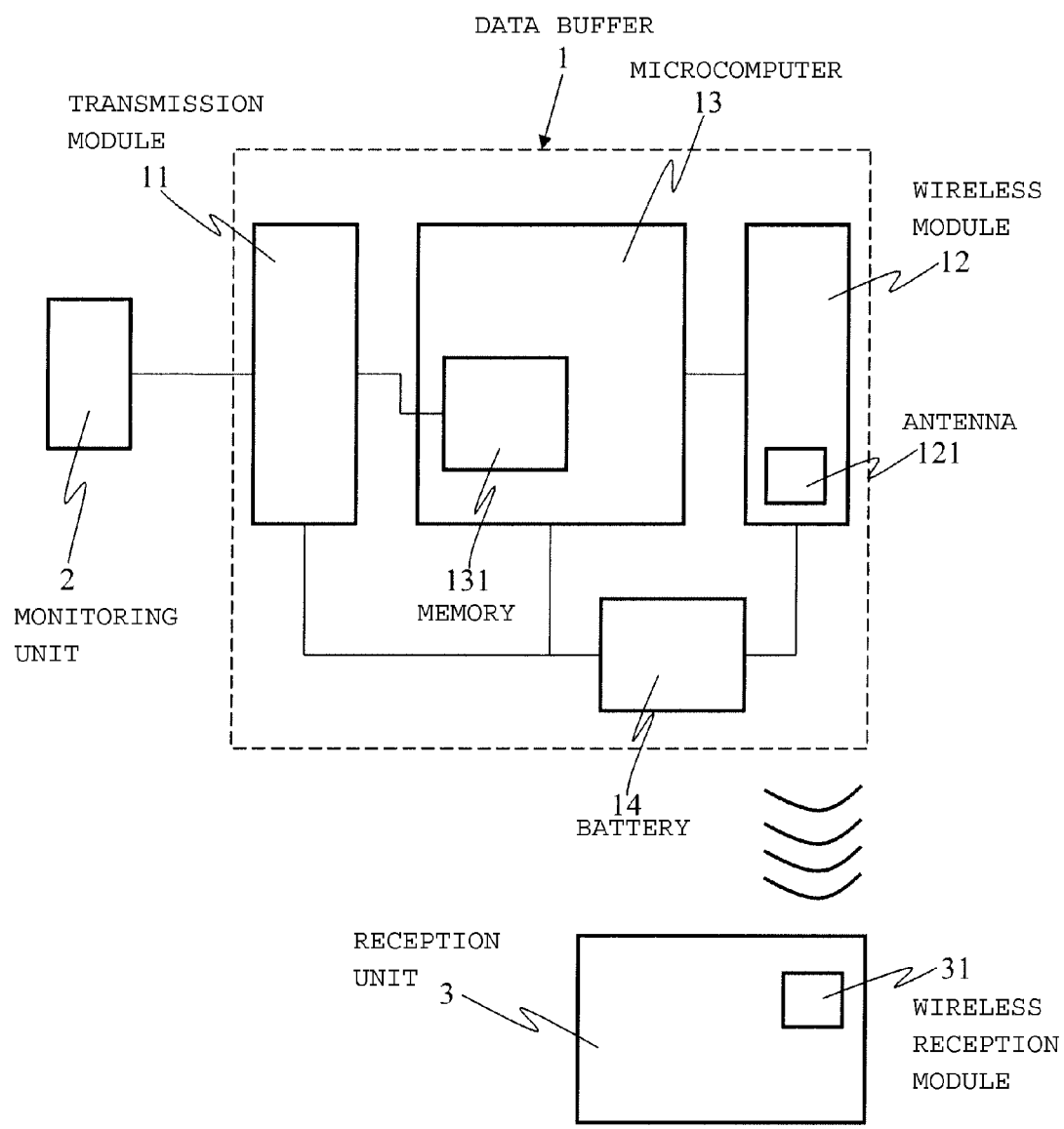

DATA BUFFER APPARATUS WITH WIRELESS TRANSMISSION FUNCTION

CROSS-REFERENCED TO RELATED APPLICATIONS

This Non-provisional application claims priority under 35 U.S.C. §119(a) on Patent Application No(s). [099134047] filed on Oct. 6, 2010, Republic of China, the entire contents of which are hereby incorporated by reference.

FIELD OF THE INVENTION

The present invention relates to a data buffer apparatus; particularly, an apparatus that can receive and buff the signals gained by a monitoring device, and send the signals wirelessly to a wireless reception apparatus.

BACKGROUND OF THE INVENTION

With the improvement of medication, people can collect and analyze the vital signs, such as body temperature, blood pressure, blood sugar, pulse, respiration rate, and EEG to learn more about the messages sent by a body. Therefore, there are many relevant measuring tools, such as blood-pressure meter and electrocardiograph, on the market. These apparatuses can provide users the convenience of taking these vital signs at any time and any place, to understand the status of one's own body. However, in medical field, there are many diseases take a long time to note the occurrences of symptoms. For example the heart disease, the obstructive Sleep Apnea Syndrome, and some other chronic sleep relevant problems takes a long time to observe all kinds of vital signs to evaluate the transition of the status of diseases to further control the changes in the diseases. However, current physical signal monitoring systems are constructed on the base of the traditional wire transmission technology. The facilities are often really large and stationary. Moreover, users have to be covered with wires to be monitored. As a result, the subjects' movement is largely limited. On the other hand, even though current meters on the market are small and portable, they can only be used stand-alone. Therefore, the function of long term monitoring the status of a disease or real-time monitoring is lacked; hence, the effect of the use is limited. However, if data transmission is needed, the devices will need to be largely modified, so that very few products would be equipped with the function of network transmitting, which is very bad for the establishment of distance medication in the future.

In conclusion, the modification of long term or real-time monitoring device needs to be done as soon as possible. With the growing emphasis on the needs of distance medication and the global aging population, how to modify current meters on the market under the premise of the least changes and lowest costs to provide it a meter that can monitor disease long term and immediately, and the functions of automatic transmission, high quality individual monitoring are the main focuses.

Due to the shortness of prior art, the applicant of the present invention finally figured out the idea to overcome the shortness of prior art through a lot of careful experiments and research with restless spirit.

SUMMARY OF THE INVENTION

The major goal of the present invention is to provide a data buffer apparatus that has the function of wireless transmission. To solve the problems caused by the meters of the prior art that can not monitor the status of disease long term or immediately through this design.

In order to achieve the goal disclosed above, the present invention provides a data buffer apparatus with wireless transmission, including: a transmission interface module, coupled to a monitoring unit and receiving at least a signal data that are continuously measured by the measuring unit; a memory module, coupled to the transmission interface module and can store the signal data; a wireless transmission module, used to establish wireless connection, and transmits the signal data to a reception unit through a wireless method; and a microprocessor module, coupled to the memory module and the wireless transmission module; wherein, when the memory module is stored with the signal data, the microprocessor module will control the wireless transmission module to attempt to establish wireless connection. If wireless connection is established successfully, the signal data stored in the memory module are sent to the reception unit through the wireless method. If not, the microprocessor module will attempt to establish wireless connection again after a period of time.

Another goal of the present invention is that the memory module of the data buffer apparatus is a FIFO memory.

Yet another goal of the present invention is that the transmission interface module of the data buffer apparatus is UART.

The techniques, means and effects of the present invention will be further described with preferred embodiments and drawings in the following sections.

BRIEF DESCRIPTION OF THE DRAWINGS

FIG. 1 schematically illustrates the block diagram showing the functions of the data buffer apparatus with wireless transmission of the present invention.

DETAILED DESCRIPTION OF THE INVENTION

Please refer to FIG. 1, FIG. 1 schematically illustrates the block diagram showing the functions of the data buffer apparatus with wireless transmission of the present invention. The data buffer apparatus 1 having wireless transmission of the present invention includes a transmission interface module 11, a wireless transmission module 12, a microprocessor module 13 and a battery module 14. The transmission interface module 11 is coupled to a monitoring unit 2, and the monitoring unit 2 can continuously measure at least a signal data. The signal data can be physiological signal, such as body temperature, blood pressure, blood sugar, pulse, electrocardiogram, respiration or EEG. For example, how many pulses per minute, the fluctuation of body temperature in an hour and other long term monitoring and statistics data, or other immediate monitoring data. The signal data of the present invention is not limited to physiological signal. The signal data of the present invention can also include other signal. Moreover, the monitoring unit 2 can be a hemadynamometer, blood sugar meter, thermometer, palpitation meter, electrocardiogram or physiological sensing meter, etc. The signal data measured by the monitoring unit 2 is transmitted to the data buffer apparatus 1 through the transmission interface module 11, and the signal data are stored in a memory module 131 of the microprocessor module 13 and the memory module 131 is coupled to the transmission interface module 11; more particularly, the memory module 131 can be a FIFO memory, which can buff the signal data transmitted from the transmission interface module 11. The transmission interface module 11 particularly can be the interface of UART, which is the interface commonly used in most health monitoring apparatus. However, the interface of the present invention is not limited to this. The microprocessor module 13 is coupled to the memory module 131 and the wireless transmission module 12. The wireless transmission module 12 is used to establish wireless connection. The wireless transmission module 12 further includes an antenna 121, and transmits the signal data to a reception unit 3 through a wireless method. The reception unit 3 includes a wireless reception module 31, which can establish a wireless connection with the wireless transmission module 12 to receive the signal data. The reception unit 3 can particularly be a computer or a microcomputer system that can be connected to the Internet or network. Moreover, the wireless transmission module 12 can particularly be an wireless RF module, such as RF, WIFI, Bluetooth or WiMax. However, the reception unit 3 and the wireless transmission module 12 of the present invention are not limited to the examples mentioned above; when the memory module 131 is stored with the signal data, the microprocessor module 13 controls the wireless transmission module 12 to attempt to establish wireless connection. If wireless connection is successfully established, the signal data stored in the memory module 131 will be sent to the reception unit 3 through the wireless method. If not, the wireless transmission module 12 will attempt to establish wireless connection again after a period of time; and the signal data will be transmitted after the wireless connection is successfully established. Moreover, according to the characteristics of FIFO of the memory, the data sent in first to be processed will be sent out first. When the wireless connection can not be established, the signal data will be buffed in the memory module 131, until the wireless connection between the wireless transmission module 12 and the wireless reception module 31 is established; these modules in the data buffer apparatus 1 can be provided power through the battery module 14 in the data buffer apparatus 1.

Therefore, specifically speaking, the data buffer apparatus 1 may have three operation mode: mode 1 is a sleeping mode, that is when there is no signal data in the memory module 131, the wireless transmission module 12 will be turned off; the overall power consumption of the whole circuit is close to zero, less than 10 mAmp; mode 2 is a standby mode, that is when the memory module 131 receives the signal data transmitted from the monitoring unit 2, the data buffer apparatus 1 will attempt to establish wireless connection and during the time period, the power consumption will be higher than sleeping mode but remain low, such as lower than 20 mAmp; mode 3 is data transmission mode, when the wireless connection is successfully established, the data buffer apparatus 1 can transmit the signal data collected to another computer or microprocessor system through the wireless transmission module 12 at high speed. During the time period, the power consumption reaches its peak, but the time of the high power consumption is not long due to fast speed transmission. After the data buffer apparatus 1 has finished signal data transmission, it then again enters the sleeping mode. The three operation modes above implement the functions of automatic transmission and buff.

To conclude, the data buffer apparatus 1 provides wireless transmission function using UART interface which is installed in most health monitoring systems with very small scale of modification; and if the reception unit 3 where the other wireless reception module 31 is at, which receives signal data from the wireless transmission module 12, has access to the Internet or network, the signal data can be uploaded automatically to the Internet or network, hospitals or designated servers to be further processed, analyzed and used to provide precaution. Therefore, health monitoring industry can easily establish a set of Internet health monitoring systems, which is very advantageous to the establishment of distance medication, and the costs and time spent required are much lower and shorter than developing a new product, which is very business friendly. As a result, users can also gain high quality monitoring capability with low costs, such as chronic diseases, long-term therapy, long-term rehabilitation and other long term medication for the patients who need long term monitoring. Therefore, the data buffer apparatus 1 is established using all kinds of well-developed physiological message collectors, through wireless transmission and Internet transmission system. The data buffer apparatus 1 has the following characteristics: use friendly, automatic transmission, long term medication and care; particularly, chronic diseases, long term therapy, long term rehabilitation or the long term monitoring for a healthy person, elderly, child, occasionally ill person, or middle age people who want to prevent any potential diseases, which solves the problems caused by the traditional monitoring apparatus that can not monitor the status of diseases for a long period of time or immediately.

The embodiments above are only used to illustrate the spirit and the effects of the present invention instead of limiting the scope of the present invention. Therefore, a skilled person in the art can modify the above embodiments without departing from the spirit of the present invention. The scope of the present invention should be defined by the following claims.

What is claimed is:

1. A data buffer apparatus with wireless transmission for coupling to a health monitor by a UART interface, including:
   a UART interface module, coupled to the health monitor with the UART interface and receiving at least a signal data that are continuously measured by the health monitor;
   a FIFO memory module, coupled to the UART interface module for storing the signal data;
   a wireless transmission module, used to establish a wireless connection, for transmitting the signal data to a reception unit through a wireless method;
   a battery module to provide power to the data buffer apparatus; and
   a microprocessor module, coupled to the FIFO memory module and the wireless transmission module, only processes data transmission and power consumption of the battery module; wherein, when the FIFO memory module is stored with the signal data, the microprocessor module controls the wireless transmission module to attempt to establish the wireless connection;
   if the wireless connection is established successfully, the signal data sent in first to be processed is sent out first to the reception unit through the wireless connection from the FIFO memory module;
   if the wireless connection is not successfully established, the microprocessor module will attempt to establish the wireless connection again after a period of time, the signal data is buffered in the FIFO memory module;
   wherein a first level of power is used when the wireless connection is successful and a second lower level of power is used when the wireless connection is not successful.

2. The data buffer apparatus according claim 1, wherein the wireless transmission module is a wireless module including one of RF, WIFI, Bluetooth or WiMax.

3. The data buffer apparatus according claim 1, wherein the health monitor is one of a hemadynamometer, blood sugar meter, thermometer, palpitation meter, electrocardiogram or physiological sensing meter.

4. The data buffer apparatus according claim 1, wherein the reception unit includes a wireless reception module, which establishes the wireless connection with the wireless transmission module for receiving the signal data.

5. The data buffer apparatus according claim 4, wherein the reception unit is a computer or a microcomputer system that is connected to the network.

6. The data buffer apparatus according claim 1, wherein the data buffer apparatus has three operation modes:
   mode 1 is a sleeping mode, when there is no signal data in the FIFO memory module, the battery module consumption is lower than 10 mAmp;
   mode 2 is a standby mode, when the data buffer apparatus attempts to establish the wireless connection or during the period of time, the battery module consumption is lower than 20 mAmp;
   mode 3 is data transmission mode, when the data buffer apparatus transmits the signal data to the reception unit, the battery module consumption reaches its peak;
   after the data buffer apparatus has finished signal data transmission, the data buffer apparatus enters the sleeping mode.

7. The data buffer apparatus according claim 1, wherein the wireless transmission module further includes an antenna.

8. The data buffer apparatus according claim 1, wherein the signal data is a physiological signal, including one of a body temperature, blood pressure, blood sugar, pulse, electrocardiogram, respiration or EEG.

* * * * *